(12) United States Patent
Hase

(10) Patent No.: US 12,740,783 B2
(45) Date of Patent: Sep. 22, 2026

(54) TREATMENT TOOL

(71) Applicant: Olympus Corporation, Tokyo (JP)

(72) Inventor: Hidenosuke Hase, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 18/920,593

(22) Filed: Oct. 18, 2024

(65) Prior Publication Data

US 2025/0040929 A1 Feb. 6, 2025

Related U.S. Application Data

(63) Continuation of application No. 18/056,687, filed on Nov. 17, 2022, now Pat. No. 12,167,851, which is a continuation of application No. PCT/JP2020/021673, filed on Jun. 1, 2020.

(51) Int. Cl.
*A61B 17/29* (2006.01)
*A61B 17/072* (2006.01)

(52) U.S. Cl.
CPC .................. *A61B 17/07207* (2013.01); *A61B 2017/2927* (2013.01)

(58) Field of Classification Search
CPC ...... A61B 17/07207; A61B 2017/2927; A61B 18/1445; A61B 2017/00477; A61B 2017/2929; A61B 2018/00589; A61B 2018/0063; A61B 2018/00994; A61B 17/320068
USPC ......... 227/175.1–182.1, 8, 19; 606/139, 142, 606/143, 205–208
See application file for complete search history.

(56) References Cited

U.S. PATENT DOCUMENTS

| | | | | |
|---|---|---|---|---|
| 2,643,581 | A * | 6/1953 | Wehrenfennig | G03B 17/12 285/376 |
| 2,972,493 | A * | 2/1961 | Waters | G05G 1/12 403/354 |
| 3,069,875 | A | 12/1962 | Crum, Jr. | |
| 3,161,242 | A * | 12/1964 | Etzkorn | B25D 17/005 173/109 |
| 3,211,485 | A | 10/1965 | Petersen | |

(Continued)

FOREIGN PATENT DOCUMENTS

| | | | | |
|---|---|---|---|---|
| CA | 2192285 | A1 * | 6/1997 | B25B 23/0035 |
| CA | 2673618 | C * | 10/2012 | B23Q 5/045 |

(Continued)

OTHER PUBLICATIONS

U.S. Appl. No. 18/056,687, filed Nov. 17, 2022, Treatment Instrument.
"U.S. Appl. No. 18/056,687, Final Office Action mailed May 7, 2024", 16 pgs.
"U.S. Appl. No. 18/056,687, Non Final Office Action mailed Jan. 16, 2024", 17 pgs.

(Continued)

*Primary Examiner* — Robert F Long
(74) *Attorney, Agent, or Firm* — Schwegman Lundberg & Woessner, P.A.

(57) ABSTRACT

A treatment tool can include an end effector comprising an ultrasonic blade, a tubular portion coupled to the end effector, and a driver coupled to a proximal end of the tubular portion. The driver can be configured to actuate the end effector via the tubular portion. The treatment tool can further include a pusher configured to support a coupling between the tubular portion and the driver in order to prevent a movement of the tubular portion in a longitudinal direction thereof.

15 Claims, 11 Drawing Sheets

(56) References Cited

U.S. PATENT DOCUMENTS 3,532,368 A * 10/1970 Stuart ........................ F16B 1/00 24/305
3,823,474 A 7/1974 Ionescu
3,873,863 A * 3/1975 Pew ........................ H02K 7/145 310/90
3,894,706 A * 7/1975 Mizusawa ............... F16L 3/237 248/68.1
4,114,927 A * 9/1978 Butcher ................ F16L 37/086 285/317
4,179,632 A 12/1979 Harvell
4,402,626 A * 9/1983 Recker .................... F16D 1/116 403/328
4,413,937 A * 11/1983 Gutsche .................... B25F 3/00 408/239 R
4,460,296 A * 7/1984 Sivertson, Jr. ........ B25B 33/005 408/239 R
4,930,954 A * 6/1990 Dague ................ B23Q 11/1084 409/218
4,971,161 A 11/1990 Godell
5,151,101 A 9/1992 Grossi et al.
5,163,598 A 11/1992 Peters et al.
5,257,771 A * 11/1993 Portis ...................... F16K 31/14 251/293
5,263,249 A * 11/1993 Kaywood ............... F01L 1/047 74/567
5,695,504 A 12/1997 Gifford, III et al.
5,765,652 A * 6/1998 Mathis .................... B25F 5/001 173/217
5,782,807 A * 7/1998 Falvai .............. A61M 25/0668 604/164.1
5,795,232 A * 8/1998 Sitzberger ................ F16D 3/74 464/81
5,823,499 A * 10/1998 Ito .......................... B60N 2/067 464/57
5,992,538 A * 11/1999 Marcengill .......... B25D 11/102 173/171
6,006,434 A 12/1999 Templeton et al.
6,035,515 A * 3/2000 Baer ...................... H02K 15/00 29/525
6,056,735 A 5/2000 Okada et al.
6,213,672 B1 * 4/2001 Varga ....................... B25G 1/04 403/109.1
6,214,017 B1 * 4/2001 Stoddard ........ A61B 17/320068 606/128
6,228,059 B1 * 5/2001 Astarita ............. A61B 17/3421 604/165.01
6,305,867 B1 10/2001 Schweigert et al.
6,394,717 B1 * 5/2002 Mazaki .................. B28D 1/041 408/124
6,464,588 B1 * 10/2002 Rupp ........................ F16F 1/16 464/179
6,516,896 B1 * 2/2003 Bookshar .............. B23P 19/066 173/217
6,546,596 B2 * 4/2003 Grote .................. B05C 17/0205 16/113.1
6,938,587 B2 9/2005 Thomas et al.
7,004,668 B2 * 2/2006 Lombardo ................ F16C 1/08 403/333
7,300,077 B2 * 11/2007 Tawara .................... B25G 3/26 403/378
7,739,800 B2 6/2010 Hurley et al.
8,109,183 B2 * 2/2012 Santamarina ....... B25B 23/1405 81/477
8,220,366 B1 * 7/2012 Fierro ..................... B25B 13/06 81/177.85
8,333,721 B2 12/2012 Makin et al.
8,453,914 B2 6/2013 Laurent et al.
8,485,488 B2 * 7/2013 Forrest ................... A47C 7/002 248/407
8,490,852 B2 7/2013 Viola
9,795,380 B2 10/2017 Shelton, IV et al.
9,955,966 B2 5/2018 Zergiebel
9,980,730 B2 5/2018 Sgroi
10,022,126 B2 7/2018 Sgroi, Jr.
10,039,549 B2 8/2018 Williams et al.
10,085,744 B2 10/2018 Williams et al.
10,117,655 B2 11/2018 Scirica et al.
10,117,656 B2 11/2018 Sgroi, Jr. et al.
10,130,364 B2 11/2018 Beaupréet al.
10,285,694 B2 5/2019 Viola et al.
10,314,581 B2 6/2019 Campbell
10,441,120 B1 * 10/2019 Sgroi, Jr. ................. B25G 1/04
10,478,185 B2 11/2019 Nicholas
10,709,315 B2 * 7/2020 Gavalis .............. A61B 1/00133
10,765,442 B2 9/2020 Strobl
10,874,393 B2 12/2020 Satti, III et al.
10,973,518 B2 4/2021 Calderoni
11,000,281 B2 5/2021 Stamp
11,020,112 B2 6/2021 Shelton, IV et al.
11,027,400 B2 * 6/2021 Raskin ...................... F16D 1/10
11,058,424 B2 * 7/2021 Shelton, IV ..... A61B 17/07207
11,317,936 B2 * 5/2022 James .................... A61B 90/98
11,350,939 B2 6/2022 Sgroi, Jr. et al.
11,627,959 B2 4/2023 Shelton, IV et al.
11,690,624 B2 7/2023 Eisinger
11,819,209 B2 11/2023 Prema Mohanasundaram et al.
11,857,186 B2 1/2024 Satti, III et al.
2002/0002369 A1 * 1/2002 Hood .................... A61F 9/0133 606/5
2004/0074344 A1 * 4/2004 Carroll ................ B25B 23/0021 81/121.1
2004/0094663 A1 * 5/2004 McVaugh ............... B64F 1/226 244/50
2005/0016744 A1 * 1/2005 Miyakawa .............. E02F 3/966 173/124
2005/0135890 A1 * 6/2005 Bauman .................. B23B 51/12 408/239 R
2006/0102697 A1 * 5/2006 Nagai ................. F16H 25/2021 228/101
2006/0259054 A1 11/2006 Masuda et al.
2008/0172051 A1 7/2008 Masuda et al.
2008/0216275 A1 * 9/2008 Collinet ................ B60S 1/0444 15/250.31
2009/0088742 A1 * 4/2009 Masuda ......... A61B 17/320092 606/48
2009/0281554 A1 11/2009 Viola
2010/0213240 A1 8/2010 Kostrzewski
2011/0006102 A1 1/2011 Kostrzewski
2011/0188928 A1 * 8/2011 West ....................... B23P 11/00 403/291
2012/0116363 A1 * 5/2012 Houser .................. G16H 20/40 606/1
2012/0116391 A1 5/2012 Houser et al.
2012/0174416 A1 * 7/2012 Nelson, II .............. A01G 3/085 30/276
2012/0234895 A1 9/2012 Oconnor et al.
2014/0110456 A1 4/2014 Taylor
2014/0263541 A1 9/2014 Leimbach et al.
2014/0324015 A1 10/2014 Romoscanu
2015/0053749 A1 * 2/2015 Shelton, IV ........... G16H 40/63 227/181.1
2015/0108863 A1 * 4/2015 Kubo ........................ F16D 3/64 310/103
2015/0272560 A1 10/2015 Baldwin
2015/0272575 A1 10/2015 Leimbach et al.
2016/0015374 A1 * 1/2016 Gifford .............. A61B 17/3439 600/201
2016/0051259 A1 2/2016 Hopkins et al.
2016/0062300 A1 * 3/2016 Takagi ................. G03G 15/757 464/157
2016/0106418 A1 4/2016 Shi et al.
2016/0120586 A1 5/2016 Spycher et al.
2016/0192934 A1 * 7/2016 Williams ........... A61B 17/1155 29/451
2016/0199073 A1 * 7/2016 Nino .................. A61B 17/3496 606/184
2016/0348731 A1 * 12/2016 Knuth ....................... F16D 3/16
2016/0361057 A1 12/2016 Williams
2017/0281187 A1 10/2017 Shelton, IV et al.
2017/0281189 A1 10/2017 Nalagatla et al.

(56) References Cited

U.S. PATENT DOCUMENTS

| | | | | |
|---|---|---|---|---|
| 2017/0333606 | A1* | 11/2017 | Manandhar | A61B 1/00135 |
| 2018/0080254 | A1* | 3/2018 | Yuan | E05B 65/52 |
| 2018/0168633 | A1 | 6/2018 | Shelton, IV et al. | |
| 2018/0235620 | A1 | 8/2018 | Shelton, IV et al. | |
| 2018/0296213 | A1 | 10/2018 | Strobl | |
| 2018/0333169 | A1 | 11/2018 | Leimbach et al. | |
| 2018/0355919 | A1* | 12/2018 | Livengood | A01B 71/06 |
| 2018/0368847 | A1 | 12/2018 | Shelton, IV et al. | |
| 2019/0083818 | A1 | 3/2019 | Mitchell et al. | |
| 2019/0183504 | A1 | 6/2019 | Shelton, IV et al. | |
| 2019/0293041 | A1* | 9/2019 | Dong | B25F 5/001 |
| 2019/0358801 | A1* | 11/2019 | McCue | B25F 3/00 |
| 2019/0374690 | A1* | 12/2019 | Manandhar | A61B 1/0051 |
| 2020/0405292 | A1 | 12/2020 | Shelton, IV et al. | |
| 2021/0078151 | A1* | 3/2021 | Huber | B25F 5/001 |
| 2021/0153929 | A1 | 5/2021 | Oshiro et al. | |
| 2022/0265408 | A1* | 8/2022 | Altmann | A46B 9/04 |
| 2022/0355145 | A1* | 11/2022 | Oh | A62C 31/28 |
| 2023/0051981 | A1 | 2/2023 | Asahina et al. | |
| 2023/0073915 | A1 | 3/2023 | Inui et al. | |
| 2023/0082517 | A1 | 3/2023 | Hase | |
| 2024/0123593 | A1* | 4/2024 | Sattler | B23D 47/12 |
| 2024/0183476 | A1* | 6/2024 | Wenzel | F16L 37/0985 |
| 2024/0299128 | A1* | 9/2024 | Altmann | A61C 1/185 |

FOREIGN PATENT DOCUMENTS

| | | | | | |
|---|---|---|---|---|---|
| CN | 212106692 | U | * | 12/2020 | |
| CN | 112754609 | A | * | 5/2021 | F16F 15/08 |
| EP | 0779130 | A1 | * | 6/1997 | B25B 23/0035 |
| EP | 4527556 | A1 | * | 3/2025 | B25B 21/02 |
| JP | 2008178688 | A | | 8/2008 | |
| JP | 2014236984 | A | | 12/2014 | |
| JP | 2016097486 | A | * | 5/2016 | B25F 5/00 |
| JP | 2018099529 | A | | 6/2018 | |
| JP | 6495274 | B2 | | 3/2019 | |
| WO | WO-2005122918 | A1 | * | 12/2005 | A61B 17/29 |

OTHER PUBLICATIONS

"U.S. Appl. No. 18/056,687, Notice of Allowability mailed Aug. 22, 2024", 1 pg.
"U.S. Appl. No. 18/056,687, Notice of Allowance mailed Aug. 12, 2024", 11 pgs.
"U.S. Appl. No. 18/056,687, Response filed Apr. 11, 2024 to Non Final Office Action mailed Jan. 16, 2024", 12 pgs.
"U.S. Appl. No. 18/056,687, Response filed Jul. 23, 2024 to Final Office Action mailed May 7, 2024", 10 pgs.
"International Application Serial No. PCT/JP2020/021673, International Search Report dated Aug. 4, 2020", (Aug. 4, 2020), 3 pgs.

* cited by examiner 10
14
TO
13
4(2)
132
TI
141
111
Rx2
131
11
121
12
Ar1
Ar2
+Z
+Y
+X
Ax 521(52)
51
5
2
62(6)
61(6)
71
(7)
17
15
4
12
18
16
9
Rx1
10
8
14
13
Ar2
Ar1
Ax
+Z
+Y
+X 16
161
1612
1621
162
1622
163
1631
1632
1612
1611
195
193
195
19
192
192
191
194
Ax
Ar2
Ar1
14

Ax
16
1631(163)
161
195
1612
1621
(162)
(19)
192
(163)
1632
192
(19)
1612
14
Ar2
Ar1

193
192
14
Ax
12
142
(163) 195
1631
192
194
19
191
15
9
1622
1621
162

TREATMENT TOOL

CROSS-REFERENCE TO RELATED APPLICATION

This application is a continuation of and claims the benefit of priority to U.S. application Ser. No. 18/056,687, filed Nov. 17, 2022, which is a continuation of International Application No. PCT/JP2020/021673, filed on Jun. 1, 2020, the entire contents of each of which are incorporated herein by reference.

TECHNICAL FIELD

The present disclosure relates to a treatment tool.

BACKGROUND

A treatment tool can apply energy to a site to be treated in living tissue (hereinafter, referred to as a target site) to treat the target site (see, for example, Japanese Patent Application Laid-open No. 2014-236984).

A treatment tool can include a jaw that is openable and closable, an elongated inner pipe having a distal end portion connected to the jaw, a movable tubular portion connected to a proximal end portion of the inner pipe, and a movable handle that receives operation by an operator. The jaw can be opened or closed by movement of the movable tubular portion and inner pipe along a longitudinal axis according to operation on the movable handle.

An inner pipe of the treatment tool such as described in Japanese Patent Application Laid-open No. 2014-236984 can be connected to the movable tubular portion as follows.

First, an operator can fix a connection member to the proximal end portion of the inner pipe by welding. Thereafter, the operator can insert the proximal end portion into the movable tubular portion, insert a connection pin into the movable tubular portion from an outer peripheral surface of the movable tubular portion, and fixe the connection pin to the connection member. The inner pipe is thereby connected to the movable tubular portion.

SUMMARY

In some examples, a treatment tool can include: an end effector configured to implement treatment of living tissue, an operation input portion configured to receive operation by an operator, and a tubular portion provided along a longitudinal axis of the treatment tool. The tubular portion can include a first end and a second end. The first end can be connected to the end effector. The second end can include a first engagement portion. The tool can also include a driver configured to move along the longitudinal axis according to or responsive to operation of the operation input portion. The driver can include a second engagement portion configured to engage with the first engagement portion. The treatment tool can further include a pusher configured to connect the tubular portion and the driver to each other by coming into contact with the tubular portion toward a central axis of the tubular portion in a state where the first engagement portion and the second engagement portion have engaged with each other.

In some examples, a treatment tool can include an end effector configured to implement treatment of living tissue, an operation input portion configured to receive operation by an operator, and a tubular portion provided along a longitudinal axis of the treatment tool. The tubular portion can include a first end and a second end, the first end being connected to the end effector, the second end being provided with a first engagement portion. The treatment tool can further include a driver configured to move along the longitudinal axis according to or responsive to the operation on the operation input portion. The driver can include a second engagement portion configured to engage with the first engagement portion. The tool can also include a pusher configured to connect the tubular portion and the driver to each other by coming into contact with the tubular portion toward a central axis of the tubular portion in a state where the first engagement portion and the second engagement portion have engaged with each other. The pusher can include at least one of an attachment maintaining portion or a thin portion. The attachment maintaining portion can be configured to restrict movement of the pusher in a first direction opposite to an attachment direction in which the pusher is attached to the driver. The thin portion can be thinner than at least part of the pusher, the part being other than the thin portion.

In some examples, a treatment tool can include an end effector configured to implement treatment of living tissue, an operation input portion configured to receive operation by an operator, and a tubular portion provided along a longitudinal axis of the treatment tool. The tubular portion having a first end and a second end, the first end being connected to the end effector, the second end being provided with a first engagement portion. The treatment tool can further include a driver configured to move along the longitudinal axis according to or responsive to operation of the operation input portion. The driver can include a second engagement portion configured to engage with the first engagement portion and a pusher configured to connect the tubular portion and the driver to each other by coming into contact with the tubular portion toward a central axis of the tubular portion in a state where the first engagement portion and the second engagement portion have engaged with each other. The treatment tool can also include a fixing portion configured to fix the pusher to the driver.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Modes for implementing the disclosure (hereinafter, embodiments or examples) will be described hereinafter while reference is made to the drawings. The disclosure is not limited by the embodiments or examples described hereinafter. Furthermore, any portions that are the same will be assigned with the same reference sign, throughout the drawings.

Schematic Configuration of Treatment System

Figure 1:
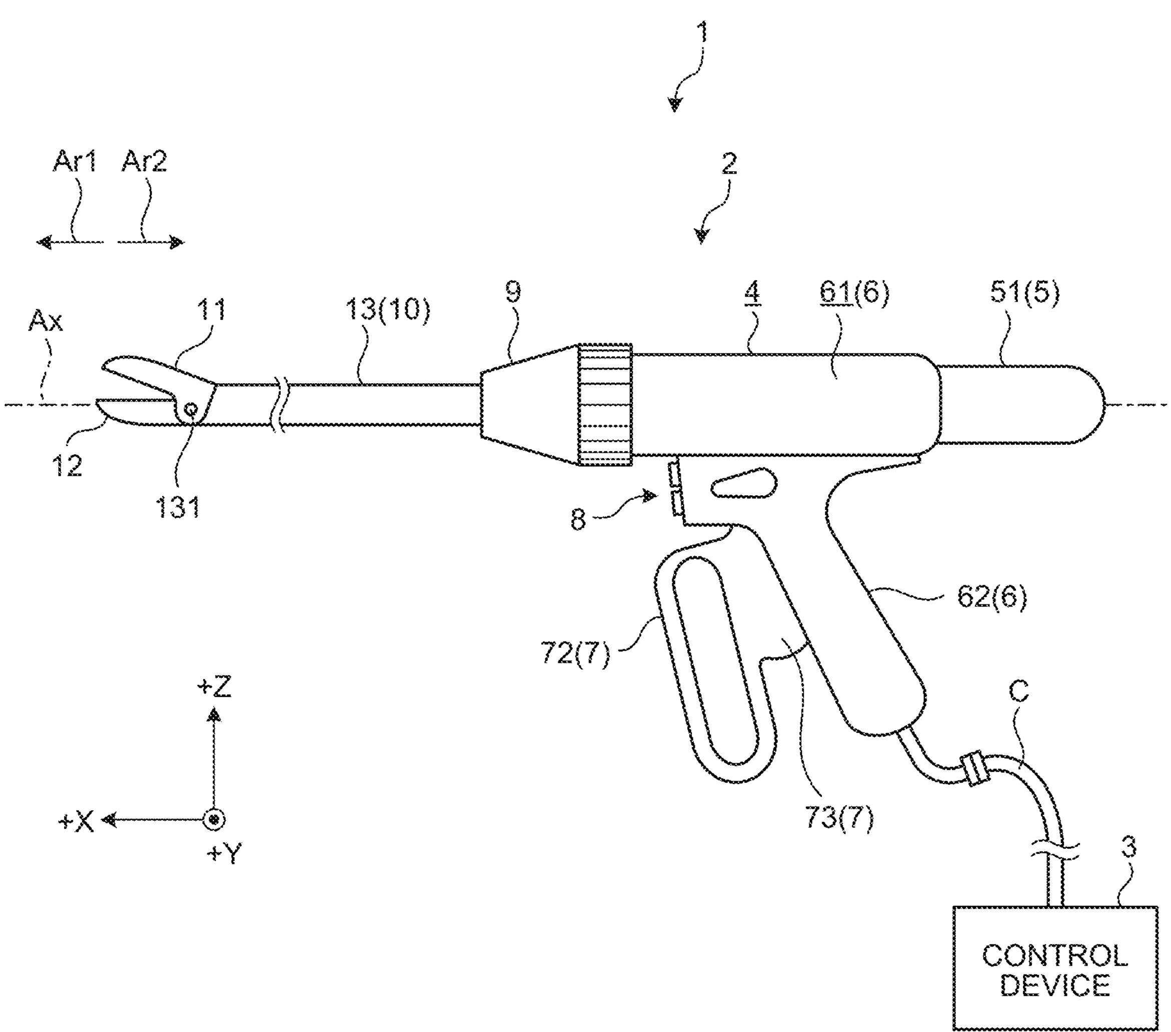
FIG. 1 illustrates an example of a diagram illustrating a treatment system according to a first embodiment.

FIG. 1 illustrates an example of a diagram illustrating a treatment system 1 according to a first embodiment.

The treatment system 1 is for applying energy such as ultrasound energy or high frequency energy to a site to be treated in living tissue (hereinafter, referred to as a target site) to treat the target site. Treatment that is able to be executed by the treatment system 1 according to the first embodiment is, for example, coagulation (sealing) of a target site, or incision of a target site. Furthermore, the treatment may also be treatment in which the coagulation and the incision are performed at the same time. The treatment system 1 can include, as illustrated in FIG. 1, a treatment tool 2 and a control device 3.

Configuration of Treatment Tool

In explanation of a configuration of the treatment tool 2, X, Y, and Z coordinate axes that are an X-axis, a Y-axis, and a Z-axis, which are orthogonal to one another, will be used hereinafter. The X-axis is an axis parallel to a central axis Ax (FIG. 1) of a sheath 10. The central axis Ax corresponds to a longitudinal axis. The Y-axis is an axis orthogonal to the plane of paper of FIG. 1. The Z-axis is an axis along a vertical direction in FIG. 1. Furthermore, one direction along the central axis Ax (in a positive direction along the X-axis) will hereinafter be referred to as a distal direction Ar1 and the other direction along the central axis Ax (in a negative direction along the X-axis) will hereinafter be referred to as a proximal direction Ar2.

Figure 2:
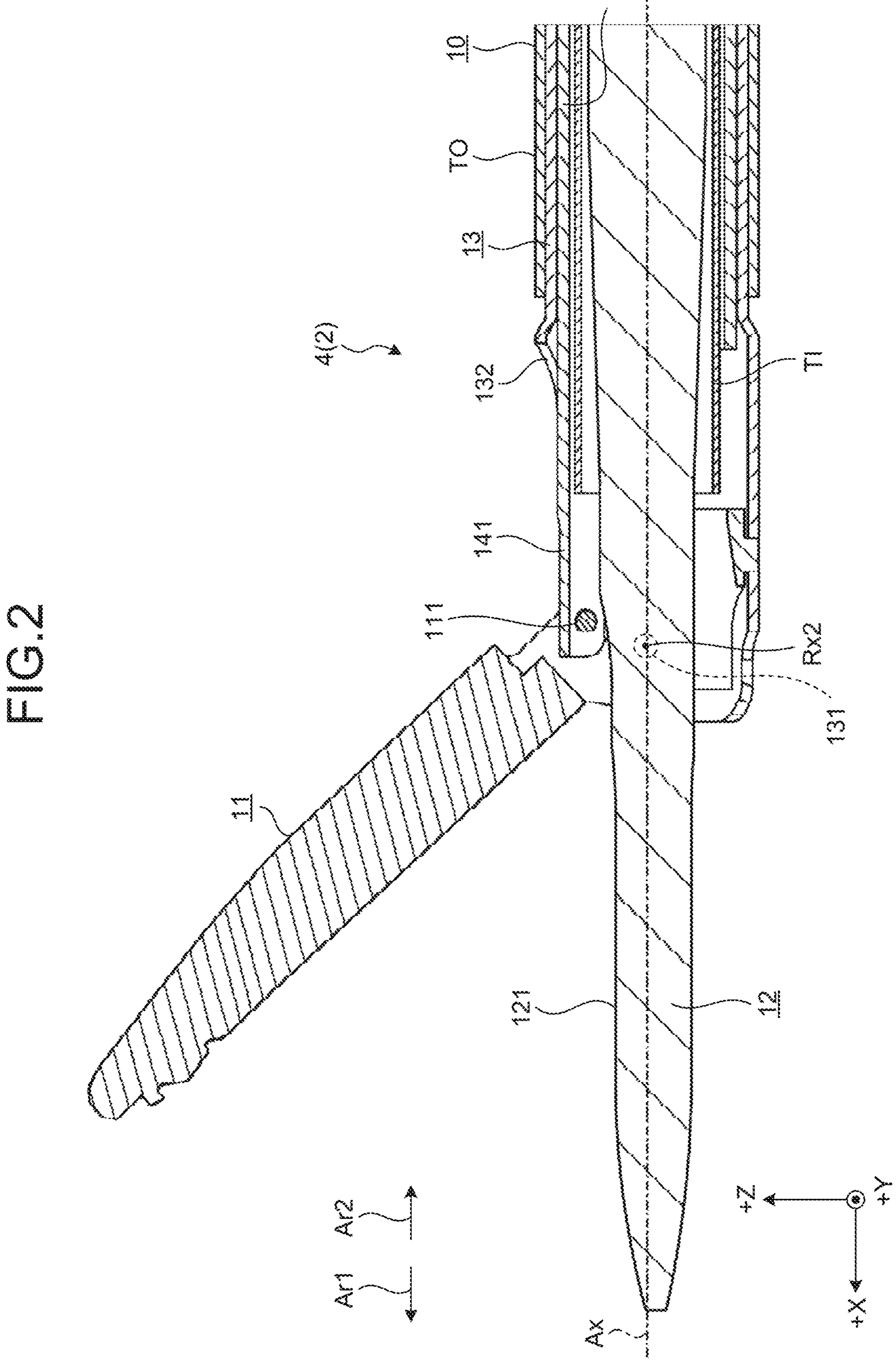
FIG. 2 illustrates an example of a diagram illustrating a configuration of a treatment tool.
Figure 3:
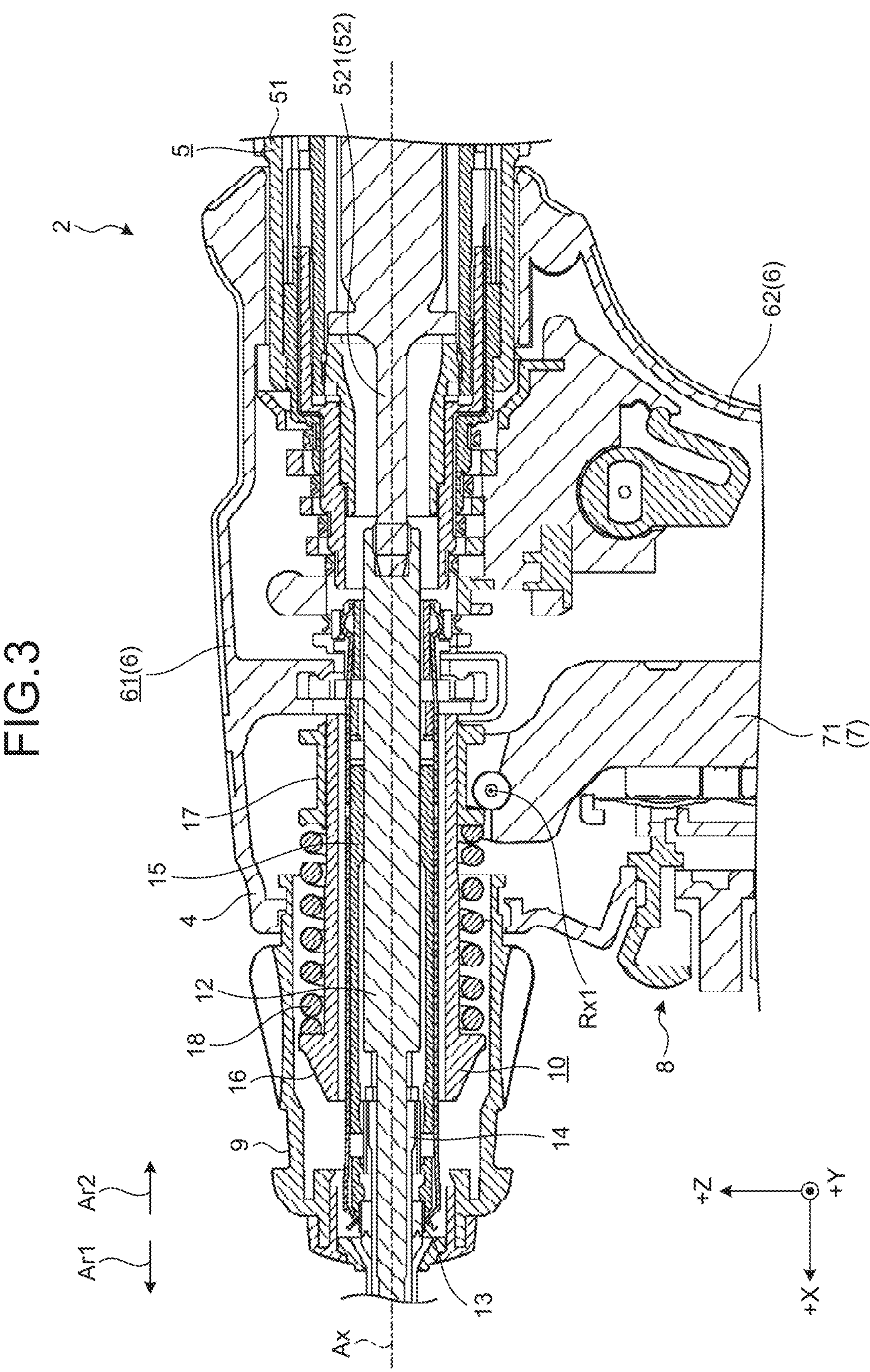
FIG. 3 illustrates an example of a diagram illustrating a configuration of the treatment tool.

FIG. 2 and FIG. 3 are diagrams illustrating the configuration of the treatment tool 2. Specifically, FIG. 2 and FIG. 3 are sectional diagrams of the treatment tool 2 cut along an X-Z plane including the central axis Ax and viewed from a positive direction along the Y-axis.

The treatment tool 2 can be an ultrasound treatment tool for treatment of a target site by application of ultrasound energy or other high frequency energy to the target site. This treatment tool 2 can include, as illustrated in FIG. 1 to FIG. 3, a handpiece 4 and an ultrasound transducer unit 5 (FIG. 1 and FIG. 3).

The handpiece 4 can include, as illustrated in FIG. 1 to FIG. 3, a holding case 6 (FIG. 1 and FIG. 3), a movable handle 7 (FIG. 1 and FIG. 3), a switch 8 (FIG. 1 and FIG. 3), a rotation knob 9 (FIG. 1 and FIG. 3), the sheath 10, a jaw 11 (FIG. 1 and FIG. 2), and a vibration transmission portion 12.

The holding case 6 can support the whole treatment tool 2. This holding case 6 can include, as illustrated in FIG. 1 or FIG. 3, a holding case body 61 that is coaxial with the central axis Ax and approximately cylindrical, and a fixed handle 62 that extends in the negative direction along the Z-axis from the holding case body 61 that can be grasped by an operator, such as an operating surgeon.

In an example, the movable handle 7 corresponds to an operation input portion. The movable handle 7 can receive each of a closing operation and an opening operation by an operator, such as an operating surgeon. The movable handle 7 can include, as illustrated in FIG. 1 or FIG. 3, a handle base portion 71 (FIG. 3), an operating portion 72 (FIG. 1), and a connection portion 73 (FIG. 1).

The handle base portion 71 can be positioned inside the holding case 6. A portion of the handle base portion 71, the portion being in a positive direction along the Z-axis, can be rotatably supported about a first rotation axis Rx1 (FIG. 3) parallel to the Y-axis, by the holding case 6. Furthermore, an end portion of the handle base portion 71, the end portion being in the positive direction along the Z-axis, can protrude in the positive direction along the Z-axis in a biforked state and can be engaged with a slider 17 of the sheath 10.

The operating portion 72 is a portion that can receive each of the closing operation and the opening operation by the operator and can be positioned outside the holding case 6, as illustrated in FIG. 1.

The connection portion 73 is a portion that can be provided to extend inside and outside the holding case 6 and can connect the handle base portion 71 and the operating portion 72 to each other.

The movable handle 7 can rotate anticlockwise in FIG. 3 about the first rotation axis Rx1 in a case where the movable handle 7 receives the closing operation by the operator. That is, the operating portion 72 can move in a direction approaching the fixed handle 62. By contrast, the movable handle 7 can rotate clockwise in FIG. 3 about the first rotation axis Rx1 in a case where the opening operation on the movable handle 7 is received. That is, the operating portion 72 can move in a direction separating from the fixed handle 62.

The switch 8 can be provided, as illustrated in FIG. 1 or FIG. 3, in a state of being exposed outside from a side surface of the fixed handle 62, the side surface being in the distal direction Ar1. The switch 8 can receive treatment operation by the operator. The treatment operation is operation for application of ultrasound energy or high frequency energy to a target site.

The rotation knob 9 can have or be formed in an approximately cylindrical shape coaxial with the central axis Ax and can be provided, as illustrated in FIG. 3, near an end of the holding case body 61, the end being in the distal direction Ar1. The rotation knob 9 can receive rotating operation by the operator. The rotating operation can rotate the rotation knob 9 about the central axis Ax, relatively to the holding case body 61. Furthermore, the rotation of the rotation knob 9 can rotate the jaw 11 and the vibration transmission portion 12 about the central axis Ax.

The sheath 10 can have or be formed in an approximately cylindrical shape. The sheath 10 can include, as illustrated in FIG. 1 to FIG. 3, an outer pipe 13, an inner pipe 14 (FIG. 2 and FIG. 3), a holding portion 15 (FIG. 3), a slider receiver 16 (FIG. 3), and the slider 17 (FIG. 3).

The outer pipe 13 can be a cylindrical pipe formed of a material, such as metal. An outer peripheral surface of the outer pipe 13 can be covered with an outer tube TO (FIG. 2) that can be electrically insulating.

Furthermore, a first pin 131 (FIG. 1 and FIG. 2) can be fixed to an end portion of the outer pipe 13, the end portion being in the distal direction Ar1, the first pin 131 extending in a direction orthogonal to the plane of paper of FIG. 1 and FIG. 2 and supporting the jaw 11 rotatably about a second rotation axis Rx2.

Furthermore, in the positive direction along the Z-axis, a notched portion 132 (FIG. 2) can be formed in the end portion of the outer pipe 13, the end portion being in the distal direction Ar1, the notched portion 132 extending from a distal end of the outer pipe 13 in the proximal direction Ar2.

In an example, the inner pipe 14 corresponds to a tubular portion. The inner pipe 14 can be a cylindrical pipe having a diameter with a dimension smaller than that of the outer pipe 13. Furthermore, the inner pipe 14 can be inserted in the outer pipe 13 in a state of being coaxial with the outer pipe 13.

An arm portion 141 that protrudes in the distal direction Ar1 can be provided, as illustrated in FIG. 2, in the inner pipe 14, the arm portion 141 being in the positive direction along the Z-axis at an end portion of the inner pipe 14, the end portion being in the distal direction Ar1. A second pin 111 can be provided in the jaw 11 and extending parallel to the second rotation axis Rx2 (the first pin 131) can be inserted in this arm portion 141.

The holding portion 15 can be formed of a material that is electrically insulating, such as resin, and can have or be formed in an approximately cylindrical shape. This holding portion 15 can be inserted in the rotation knob 9 and the holding case body 61, in a state of extending over the rotation knob 9 and the holding case body 61, as illustrated in FIG. 3. The holding portion 15 can hold the vibration transmission portion 12 that has been inserted in the holding portion 15. Furthermore, the holding portion 15 can be mechanically connected to the rotation knob 9 and the outer pipe 13 at an end portion of the holding portion 15, the end portion being in the distal direction Ar1. That is, the holding portion 15, the outer pipe 13, the jaw 11, and the vibration transmission portion 12 can rotate, together with the rotation knob 9, about the central axis Ax, according to the rotating operation on the rotation knob 9 by the operator.

The slider receiver 16 can correspond to a driver. The slider receiver 16 can be formed of a material that is electrically insulating, such as resin, and can have or be formed in an approximately cylindrical shape. The slider receiver 16 can be provided movably along the central axis Ax relatively to the holding portion 15, in a state where the holding portion 15 has been inserted in the slider receiver 16. An end portion of the slider receiver 16, the end portion being in the distal direction Ar1, can be connected to an end portion of the inner pipe 14, the end portion being in the proximal direction Ar2, in a state where the end portion of the slider receiver 16 can move along the central axis Ax relatively to the holding portion 15 but can be restricted from rotating about the central axis Ax. That is, the slider receiver 16 and the inner pipe 14 can rotate, together with the rotation knob 9, about the central axis Ax, according to the rotating operation on the rotation knob 9 by the operator.

A connection structure between the inner pipe 14 and the slider receiver 16 will be described later.

The slider 17 can have or be formed in an approximately cylindrical shape and can be provided movably along the central axis Ax, relative to the slider receiver 16, in a state where the slider receiver 16 has been inserted in the slider 17. The slider 17 can be engaged with the movable handle 7 (the end portion of the handle base portion 71, the end portion being in the positive direction along the Z-axis) as described above.

The slider 17, the slider receiver 16, and the inner pipe 14 can operate as described below, according to operations on the movable handle 7 by the operator.

In response to a closing operation on the movable handle 7 by the operator, the slider 17 can be pushed in the distal direction Ar1 along the central axis Ax by the movable handle 7 (the end portion of the handle base portion 71, the end portion being in the positive direction along the Z-axis). Furthermore, the slider receiver 16 can receive a pressing force in the distal direction Ar1 from the slider 17 via a coil spring 18 (FIG. 3) provided between the slider receiver 16 and the slider 17. The inner pipe 14 can move, in association with the slider receiver 16, in the distal direction Ar1 along the central axis Ax. The arm portion 141 can push the second pin 111 in the distal direction Ar1. The jaw 11 then rotates anticlockwise in FIG. 2 about the second rotation axis Rx2. In this rotation, because the second pin 111 also moves, in a state of maintaining a certain distance, about the second rotation axis Rx2, the arm portion 141 can move in the distal direction Ar1 while being deformed in the positive direction along the Z-axis where the notched portion 132 is provided. That is, the jaw 11 can move in a direction (a closing direction) approaching an end portion 121 (FIG. 2) of the vibration transmission portion 12, the end portion 121 being in the distal direction Ar1.

Furthermore, according to the opening operation on the movable handle 7 by the operator, the jaw 11 can rotate clockwise in FIG. 2 about the second rotation axis Rx2. That is, the jaw 11 can move in a direction (an opening direction) separating from the end portion 121 of the vibration transmission portion 12, the end portion 121 being in the distal direction Ar1.

As described above, the jaw 11 can open and close relative to the end portion 121 of the vibration transmission portion 12 according to operation on the movable handle 7 by the operator, the end portion 121 being in the distal direction Ar1 and can grip a target site between the jaw 11 and the end portion 121. The jaw 11 and the end portion 121 correspond to an end effector.

The coil spring 18 mentioned above can transmit drive force according to operation on the movable handle 7 by the operator to the slider receiver 16 and corresponds to an elastic material. The coil spring 18 can be used to maintain grip force for gripping a target site between the jaw 11 and the end portion 121 (FIG. 2) of the vibration transmission portion 12, the end portion 121 being in the distal direction Ar1. At least part of the jaw 11 can be formed of an electrically conducting material.

The vibration transmission portion 12 can be formed of an electrically conducting material and can have or be formed in an elongated shape linearly extending along the central axis Ax. Furthermore, the vibration transmission portion 12 can be inserted in the sheath 10 in a state where its end portion 121 in the distal direction Ar1 protrudes outside, as illustrated in FIG. 2. In this state, an end portion of the vibration transmission portion 12, the end portion being in the proximal direction Ar2, can be mechanically connected to the ultrasound transducer unit 5, as illustrated in FIG. 3. That is, the vibration transmission portion 12 can transmit ultrasound vibration generated by the ultrasound transducer unit 5, to its end portion 121 in the distal direction Ar1 from its end portion in the proximal direction Ar2. In this first embodiment, the ultrasound vibration is longitudinal vibration that is vibration along the central axis Ax.

An outer peripheral surface of the vibration transmission portion 12 can be covered with an inner tube TI (FIG. 2) that is electrically insulating, to provide electric insulation between: the outer pipe 13 and the inner pipe 14 and the vibration transmission portion 12.

The ultrasound transducer unit 5 can include, as illustrated in FIG. 1 or FIG. 3, a transducer (TD) case 51 and an ultrasound transducer 52 (FIG. 3). The TD case 51 can support the ultrasound transducer 52 and can be detachably connected to the holding case body 61.

The ultrasound transducer 52 can generate ultrasound vibration, under control by the control device 3. In this first embodiment, the ultrasound transducer 52 is a bolt-clamped Langevin transducer (BLT). For convenience of explanation, FIG. 3 illustrates only a front mass 521 of the ultrasound transducer 52 (BLT), the front mass 521 being connected to the end portion of the vibration transmission portion 12, the end portion being in the proximal direction Ar2.

Configuration of Control Device

The control device 3 can integrally control operation of the treatment tool 2 through an electric cable C (FIG. 1). Specifically, the control device 3 can detect the treatment operation on the switch 8 by the operator through the electric cable C. In a case where the control device 3 has detected the treatment operation, the control device 3 can apply ultrasound energy or high frequency energy to a target site gripped between the jaw 11 and the end portion 121 of the vibration transmission portion 12, the end portion 121 being in the distal direction Ar1, via the electric cable C. That is, the control device 3 can perform treatment of the target site.

For example, in applying ultrasound energy to a target site, the control device 3 can supply drive power to the ultrasound transducer 52 through the electric cable C. The ultrasound transducer 52 can thereby generate longitudinal vibration (e.g., ultrasound vibration) that is vibration along the central axis Ax. Furthermore, the longitudinal vibration can cause the end portion 121 of the vibration transmission portion 12 to vibrate at desired amplitude, the end portion 121 being in the distal direction Ar1. From the end portion 121, ultrasound vibration can be applied to the target site gripped between the jaw 11 and the end portion 121. In other words, ultrasound energy can be applied to the target site from the end portion 121.

Furthermore, for example, in applying high frequency energy to a target site, the control device 3 can supply high frequency power between the jaw 11 and the vibration transmission portion 12 through the electric cable C. High frequency electric current can thereby flow in or to the target site gripped between the jaw 11 and the end portion 121 of the vibration transmission portion 12, the end portion 121 being in the distal direction Ar1. In other words, high frequency energy can be applied to the target site.

Connection Structure Between Inner Pipe and Slider Receiver

Figure 4:
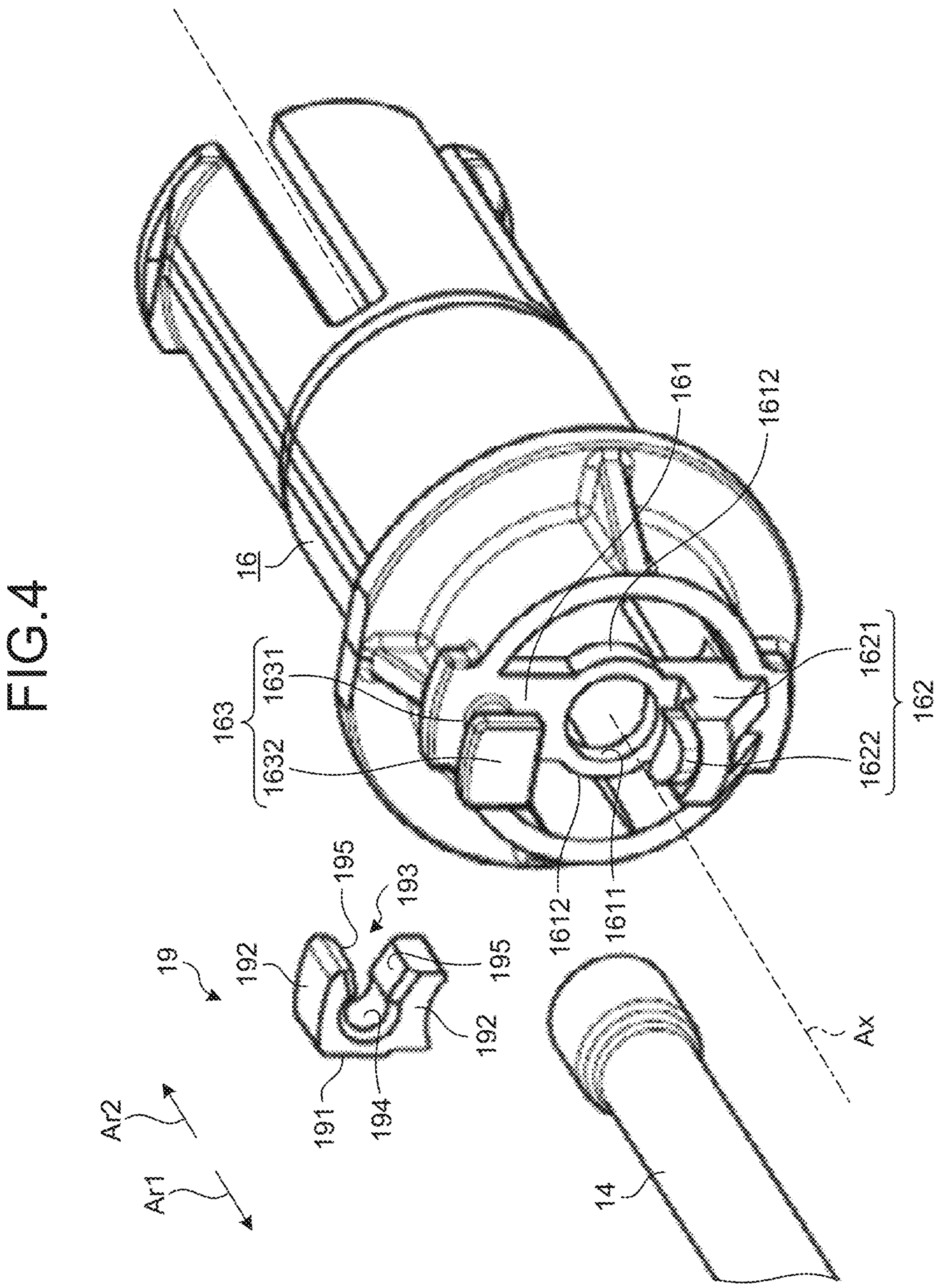
FIG. 4 illustrates an example of a diagram illustrating a connection structure between an inner pipe and a slider receiver.
Figure 5:
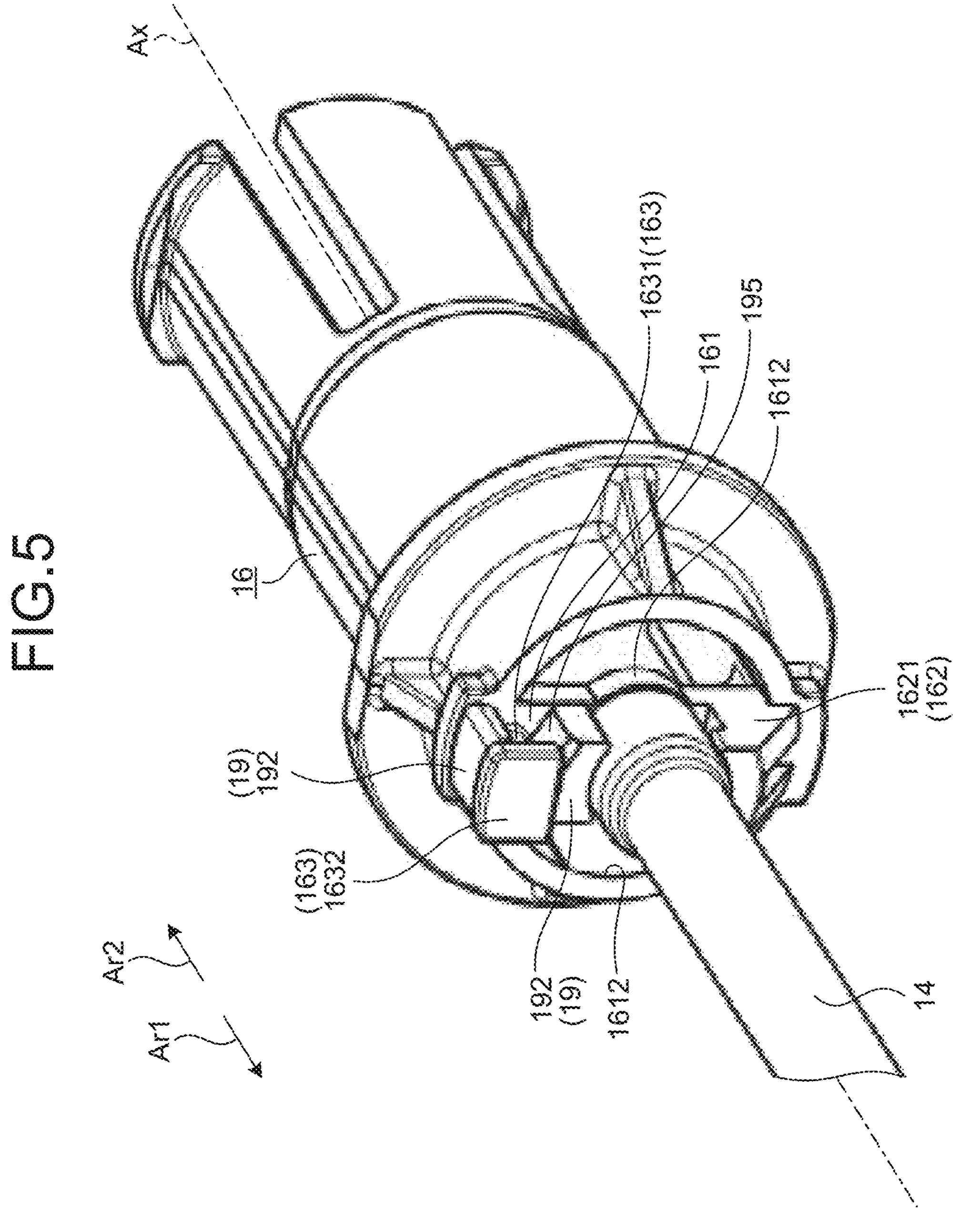
FIG. 5 illustrates an example of a diagram illustrating the connection structure between the inner pipe and the slider receiver.
Figure 6:
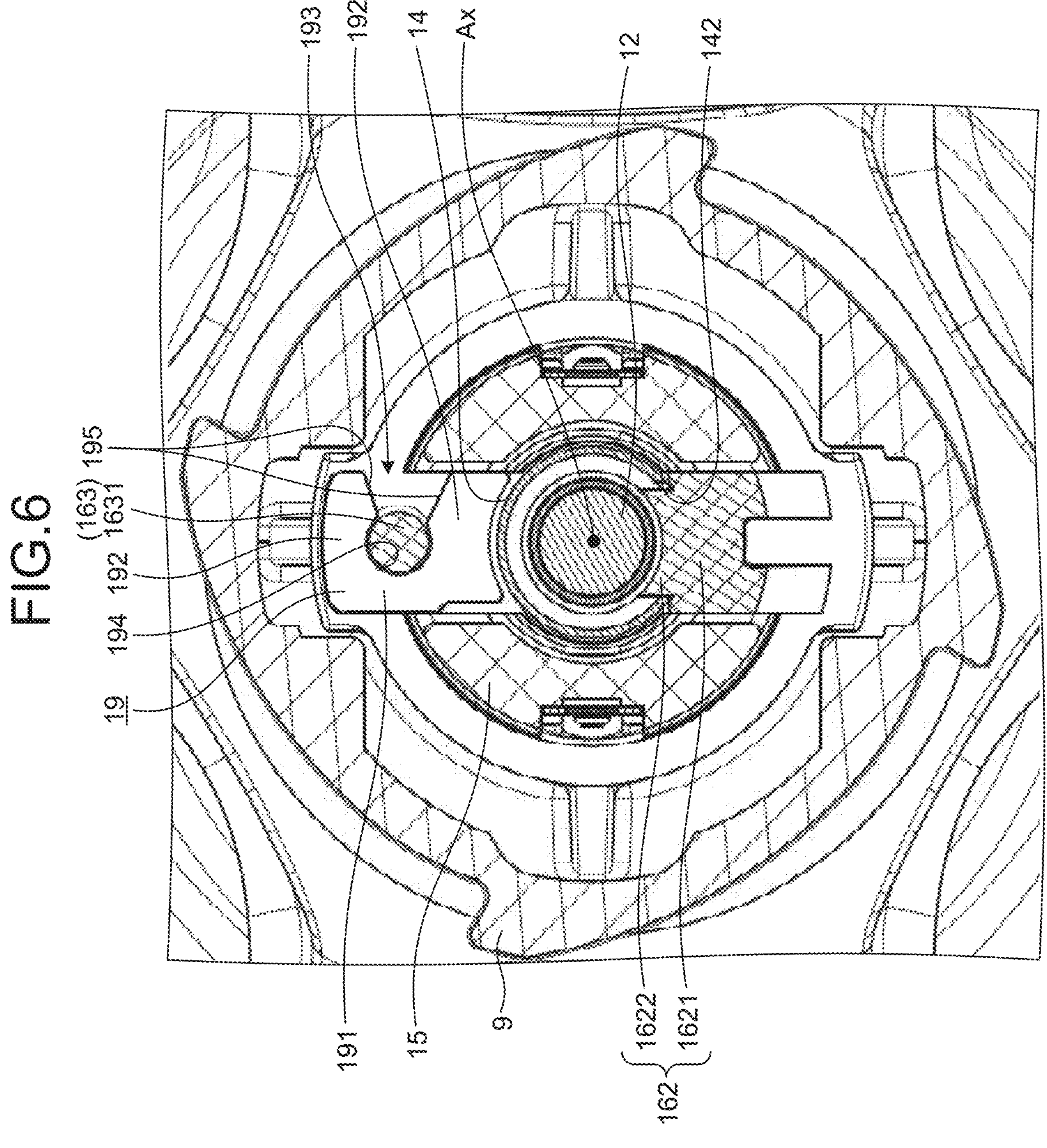
FIG. 6 illustrates an example of a diagram illustrating the connection structure between the inner pipe and the slider receiver.
Figure 7:
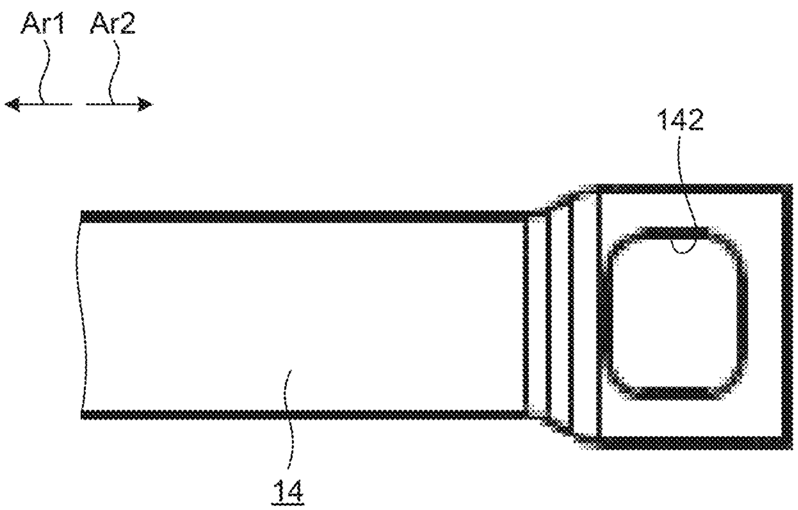
FIG. 7 illustrates an example of a diagram illustrating the connection structure between the inner pipe and the slider receiver.

The connection structure between the inner pipe 14 and the slider receiver 16 will be described next. FIG. 4 to FIG. 7 are diagrams illustrating the connection structure between the inner pipe 14 and the slider receiver 16. Specifically, FIG. 4 is an exploded perspective view of a connection between the end portion of the inner pipe 14, the end portion being in the proximal direction Ar2, and the slider receiver 16. FIG. 5 is a perspective view of a state where the end portion of the inner pipe 14, the end portion being in the proximal direction Ar2, and the slider receiver 16 have been connected to each other. FIG. 6 is a sectional diagram of the connection between the end portion of the inner pipe 14, the end portion being in the proximal direction Ar2, and the slider receiver 16, the connection being cut along a plane orthogonal to the central axis A. FIG. 7 is a diagram illustrating a first engagement portion 142 provided at the end portion of the inner pipe 14, the end portion being in the proximal direction Ar2.

The first engagement portion 142 that engages with the slider receiver 16 can be provided at the end portion of the inner pipe 14, the end portion being in the proximal direction Ar2, as illustrated in FIG. 7. In this example, the first engagement portion 142 is a notch (through hole) penetrating an outer peripheral surface and an inner peripheral surface of the inner pipe 14, the notch being approximately rectangular.

A connection base body 161, a first connection portion 162, and a second connection portion 163 can be provided at the end portion of the slider receiver 16, the end portion being in the distal direction Ar1, as illustrated in FIG. 4 to FIG. 6.

The connection base body 161 is a portion where the first and second connection portions 162 and 163 can be provided. As illustrated in FIG. 4, this connection base body 161 can have a flat plate shape, can have a plate surface orthogonal to the central axis Ax, and can bridge between portions of an inner peripheral surface of the slider receiver 16 in a posture where the connection base body 161 strides over the central axis Ax.

An insertion hole 1611 can penetrating both sides of the connection base body 161, having the central axis Ax at the center of the insertion hole 1611, and being circular can be provided at the position of the central axis Ax in the connection base body 161, as illustrated in FIG. 4. This insertion hole 1611 is a hole into which the vibration transmission portion 12 can be inserted.

Furthermore, each of a pair of holes 1612 provided between the inner peripheral surface of the slider receiver 16 and the connection base body 161 can function as a hole into which the holding portion 15 can be inserted.

The first connection portion 162 can be a portion connected to the end portion of the inner pipe 14, the end portion being in the proximal direction Ar2. The first connection portion 162 can include, as illustrated in FIG. 4 to FIG. 6, a base 1621 and a second engagement portion 1622 (FIG. 4 and FIG. 6).

The base 1621 can be a portion protruding in the distal direction Ar1 from a position on a plate surface of the connection base body 161, the plate surface being in the distal direction Ar1, the position being below the insertion hole 1611 in FIG. 4.

In an example, the second engagement portion 1622 is a projection provided on an upper surface of the base 1621 and protruding upward, in FIG. 4 and FIG. 6. A tip (an upper end surface in FIG. 4 and FIG. 6) of the second engagement portion 1622 can be formed as an arc-shaped concave curved surface having the central axis Ax at the center of the arc, to avoid the vibration transmission portion 12 inserted in the insertion hole 1611. The second engagement portion 1622 can have an outer shape slightly smaller than the inner shape of the first engagement portion 142, and can engage with or connect to the first engagement portion 142 by being fitted in the first engagement portion 142.

The second connection portion 163 can be a portion where a pusher 19 described later is connected to. This second connection portion 163 can include, as illustrated in FIG. 4 to FIG. 6, a protruding portion 1631 and a retaining portion 1632 (FIG. 4 and FIG. 5).

The protruding portion 1631 can be a portion where the pusher 19 is attached to. This protruding portion 1631 can have a columnar shape protruding in the distal direction Ar1 from a position on the plate surface of the connection base body 161, the plate surface being in the distal direction Ar1, the position being above the insertion hole 1611 in FIG. 4.

The retaining portion 1632 can be a portion that is provided on a tip (an end surface in the distal direction Ar1) of the protruding portion 1631 and that can prevent the pusher 19 from falling off the tip of the protruding portion 1631, the pusher 19 having been attached to the protruding portion 1631.

The pusher 19 can be a member that maintains a state where the second engagement portion 1622 has been fitted in the first engagement portion 142, in other words, a state where the end portion of the inner pipe 14 has been connected to the slider receiver 16, the end portion being in the proximal direction Ar2. This pusher 19 can include, as illustrated in FIG. 4 to FIG. 6, a base portion 191 (FIG. 4 and FIG. 6) and a pair of protruding portions 192. The base portion 191 can be a portion extending vertically in FIG. 4 and FIG. 6.

The pair of protruding portions 192 can be portions respectively protruding from upper and lower end portions of the base portion 191 in FIG. 4 and FIG. 6, to be approximately parallel to each other. That is, the pusher 19 can be approximately "U-shaped" overall. Furthermore, an opening in the U-shape of the pusher 19 can correspond to an opening 193.

A fitting recessed portion 194 and a pair of inclined surfaces 195 can be provided inside the U-shape of the pusher 19, as illustrated in FIG. 4 or FIG. 6. The fitting recessed portion 194 is a portion where the protruding portion 1631 is fitted in and can be formed in an arc-shaped concave curved surface following an outer peripheral shape of the protruding portion 1631.

The pair of inclined surfaces 195 can be inclined surfaces separating from each other toward the opening 193 from positions where the pair of inclined surfaces 195 are respectively in contact with the fitting recessed portion 194.

A method of connecting the inner pipe 14 and the slider receiver 16 to each other will be described next.

Firstly, an operator can fit the second engagement portion 1622 in the first engagement portion 142 while placing a proximal end of the inner pipe 14 over the plate surface of the connection base body 161, the plate surface being in the distal direction Ar1.

Subsequently, the operator can hold the pusher 19 in the operator's hand, and can place the protruding portion 1631 inside the U-shape of the pusher 19 from the opening 193. In this placement, tips of the pair of protruding portions 192 of the pusher 19 are elastically deformed in directions separating from each other with the base portion 191 being a base point, by the protruding portion 1631 sliding on the pair of inclined surfaces 195 and the pair of protruding portions 192 being pressed by the protruding portion 1631. The pusher 19 can return to the original shape, by the protruding portion 1631 being fitted in the fitting recessed portion 194. The pusher 19 is thereby attached to the protruding portion 1631. In this state, the pusher 19 is provided at a position across the inner pipe 14 from the second engagement portion 1622. By pressing the outer peripheral surface of the inner pipe 14 toward the central axis Ax, the pusher 19 can maintain the state where the second engagement portion 1622 has been fitted in the first engagement portion 142. That is, the inner pipe 14 is fixed to the slider receiver 16.

An operator can detach the inner pipe 14 from the slider receiver 16 by performing operation opposite to that in the above described connection method.

The above described first embodiment has the following effects. The inner pipe 14 and the slider receiver 16 in the treatment tool 2 according to the first embodiment can be fixed to each other just by fitting of the second engagement portion 1622 in the first engagement portion 142 and attachment of the pusher 19 to the protruding portion 1631. Therefore, in fixing the inner pipe 14 to the slider receiver 16, welding is no longer required as conventionally done and the ease of assembly is able to be improved.

The inner pipe 14 and the slider receiver 16 are structured to advance and retract along the central axis Ax. Therefore, a large force along the central axis Ax can be applied to the inner pipe 14 and the slider receiver 16. Because the above described structure is adopted for attachment of the pusher 19 to the protruding portion 1631 in the treatment tool 2 according to the first embodiment, the large force mentioned above is not applied to the pusher 19. That is, the first embodiment enables improvement in the ease of assembly and implementation of a structure that enables transmission of a drive force required for opening and closing of the jaw 11.

For the possibility of effective utilization of resources, reduction of medical waste, and reduction of medical spending, remanufacturing of treatment tools has attracted attention in recent years. Remanufacturing of a treatment tool can include disassembling a used treatment tool after treatment of a target site, cleaning the disassembled treatment tool, replacing some parts, reassembling the treatment tool, sterilizing the reassembled treatment tool, checking that the treatment tool has the performance required, and thereby enabling the treatment tool to be used again.

The pusher 19 in the treatment tool 2 according to the first embodiment can be detachably attached to the slider receiver 16. This facilitates remanufacturing of the treatment tool 2. The pusher 19 in the treatment tool 2 according to the first embodiment can be provided at the position across the inner pipe 14 from the second engagement portion 1622. Therefore, the state where the second engagement portion 1622 has been fitted in the first engagement portion 142 is able to be maintained well by just the single pusher 19. Accordingly, the number of parts is able to be reduced.

Second Embodiment

A second embodiment will be described next.

In the following description, any component that is the same as that of the above described first embodiment will be assigned with the same reference sign, and detailed description thereof will be omitted or simplified.

The second embodiment is different from the above described first embodiment in that the pusher 19 and the protruding portion 1631 are shaped differently in the second embodiment. For convenience of explanation, the pusher 19 according to the second embodiment will hereinafter be referred to as a pusher 19A. The protruding portion 1631 according to the second embodiment will be referred to as a protruding portion 1631A.

Figure 8:
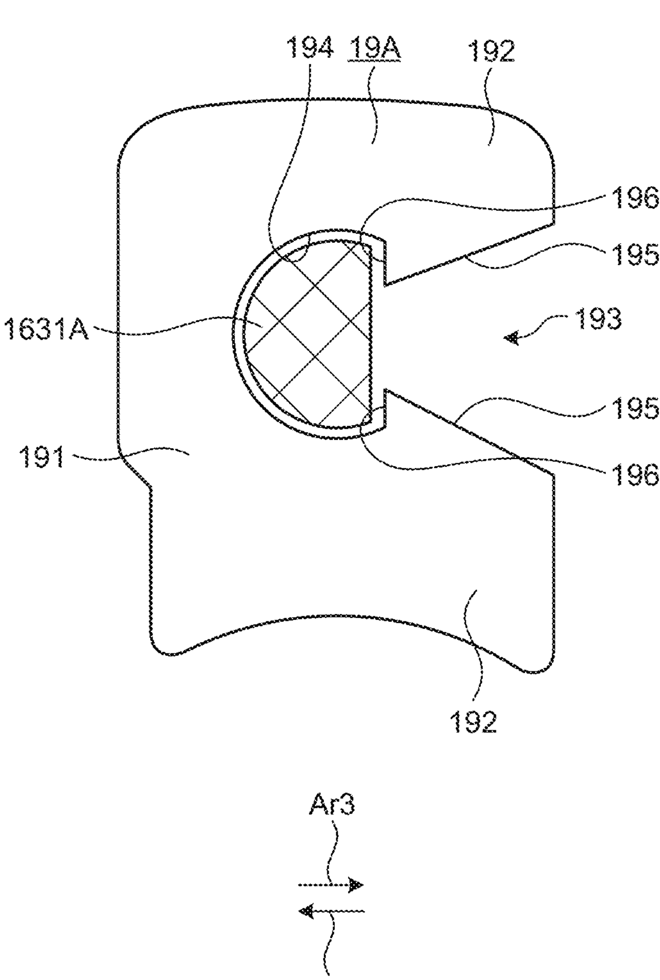
FIG. 8 illustrates an example of a diagram illustrating an attachment structure of a pusher according to a second embodiment.

FIG. 8 is a diagram illustrating an attachment structure of the pusher 19A according to the second embodiment. Specifically, FIG. 8 is a sectional view corresponding to FIG. 6.

The pusher 19A according to the second embodiment is different from the pusher 19 according to the first embodiment in that a pair of attachment maintaining portions 196 are provided in the pusher 19A, as illustrated in FIG. 8.

In an example, the pair of attachment maintaining portions 196 are portions that restrict movement of the pusher 19A in an opposite direction Ar4 opposite to an attachment direction Ar3 (FIG. 8) in which the pusher 19A is attached to the protruding portion 1631A. Specifically, the pair of attachment maintaining portions 196 can be respectively positioned at boundaries between the fitting recessed portion 194 and the pair of inclined surfaces 195, and respectively include planar portions extending in directions approaching each other and intersecting the opposite direction Ar4.

Furthermore, the protruding portion 1631A can have or be formed with a D-shaped cross section and has a surface that is planar correspondingly to the pair of attachment maintaining portions 196 described above, the surface being in the attachment direction Ar3.

That is, in this structure, the pair of attachment maintaining portions 196 can restrict movement of the pusher 19A in the opposite direction Ar4 after the protruding portion 1631A has been fitted in the fitting recessed portion 194.

The second embodiment described above has effects similar to those of the above described first embodiment.

The second embodiment has the structure in which the pair of attachment maintaining portions 196 restrict movement of the pusher 19A in the opposite direction Ar4 after the protruding portion 1631A has been fitted in the fitting recessed portion 194. Therefore, the structure makes it difficult for a person to remanufacture the treatment tool, the person being unrelated to a manufacturer that remanufactures the treatment tool.

Third Embodiment

A third embodiment will be described next.

In the following description, any component that is the same as that of the above described first embodiment will be assigned with the same reference sign, and detailed description thereof will be omitted or simplified.

This third embodiment is different from the above described first embodiment in that the pusher 19 is differently shaped. For convenience of explanation, the pusher 19 according to the third embodiment will hereinafter be referred to as a pusher 19B.

Figure 9:
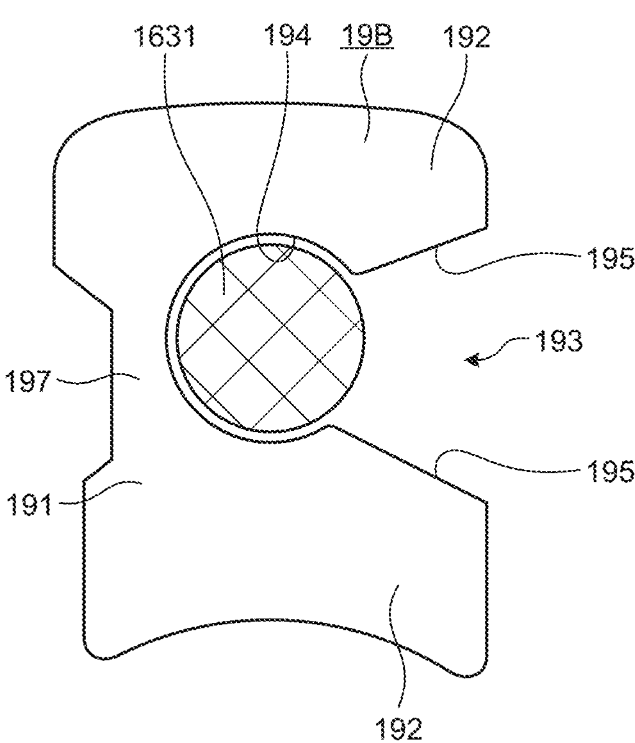
FIG. 9 illustrates an example of a diagram illustrating an attachment structure of a pusher according to a third embodiment.

FIG. 9 is a diagram illustrating an attachment structure of the pusher 19B according to the third embodiment. Specifically, FIG. 9 is a sectional view corresponding to FIG. 6.

The pusher 19B according to the third embodiment is different from the pusher 19 according to the first embodiment in that a thin portion 197 is provided in the pusher 19B, as illustrated in FIG. 9.

In an example, the thin portion 197 is a portion provided in part of the base portion 191, the part facing the opening 193 and being thinner than the other part of the base portion 191.

That is, the pusher 19B can be structured so that in a case where detachment of the pusher 19B from the protruding portion 1631 is forcedly attempted after the protruding portion 1631 has been fitted in the fitting recessed portion 194, the pusher 19B is broken from the thin portion 197.

The third embodiment described above has effects similar to those of the above described first embodiment. This third embodiment has the structure in which the pusher 19B is broken from the thin portion 197 in a case where detachment of the pusher 19B from the protruding portion 1631 is forcedly attempted after the protruding portion 1631 has been fitted in the fitting recessed portion 194. Therefore, the structure makes it difficult for a person to remanufacture the treatment tool, the person being unrelated to a manufacturer that remanufactures the treatment tool.

Fourth Embodiment

A fourth embodiment will be described next.

In the following description, any component that is the same as that of the above described first embodiment will be assigned with the same reference sign, and detailed description thereof will be omitted or simplified. The fourth embodiment is different from the first embodiment described above in that a fixing portion 20C is additionally provided in the fourth embodiment.

Figure 10:
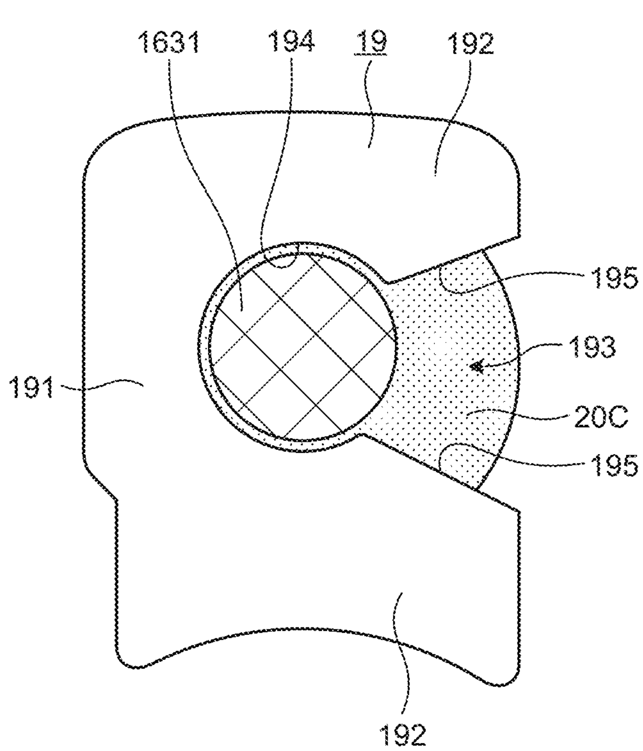
FIG. 10 illustrates an example of a diagram illustrating an attachment structure of a pusher according to a fourth embodiment.

FIG. 10 is a diagram illustrating an attachment structure of the pusher 19, according to the fourth embodiment. Specifically, FIG. 10 is a sectional view corresponding to FIG. 6.

In an example, the fixing portion 20C is a member that fixes the pusher 19 to the protruding portion 1631. In this fourth embodiment, the fixing portion 20C is an adhesive.

The fixing portion 20C can be applied between the protruding portion 1631 and the pusher 19. That is, curing the fixing portion 20C achieves a structure disabling detachment of the pusher 19 from the protruding portion 1631.

The fourth embodiment described above has effects similar to those of the above described first embodiment. The fourth embodiment has the structure in which the fixing portion 20C prevents the pusher 19 from being detached from the protruding portion 1631. Therefore, the structure enables prevention of remanufacturing of the treatment tool by a person being unrelated to a manufacturer that remanufactures the treatment tool.

Fifth Embodiment

A fifth embodiment will be described next.

In the following description, any component that is the same as that of the above described first embodiment will be assigned with the same reference sign, and detailed description thereof will be omitted or simplified. The fifth embodiment is different from the first embodiment described above in that a fixing portion 20D is additionally provided in the fifth embodiment.

Figure 11:
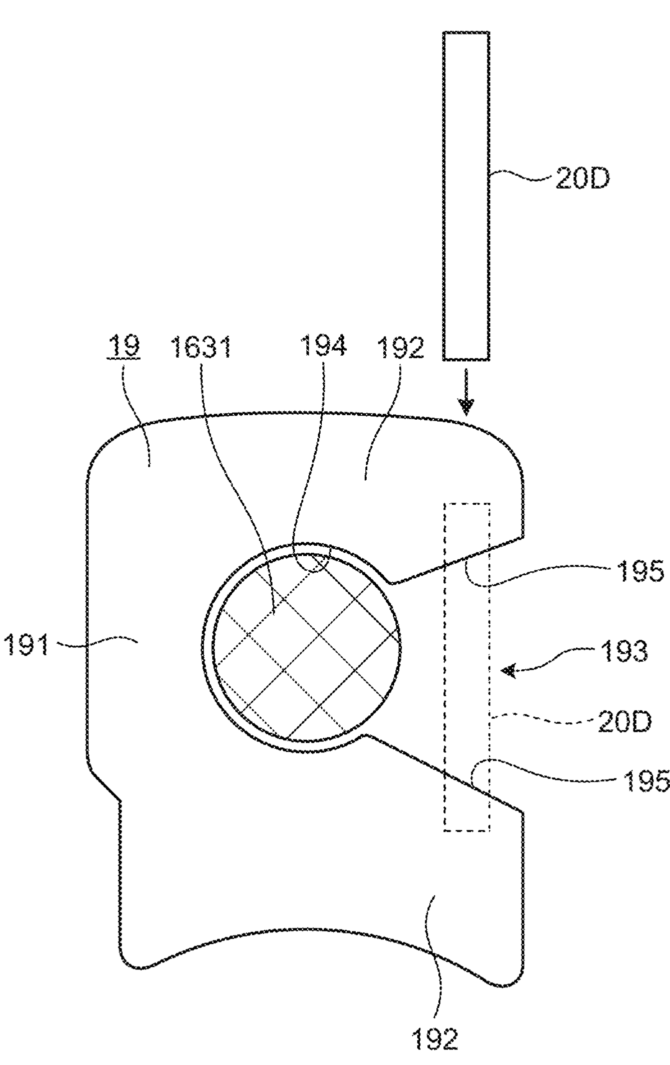
FIG. 11 illustrates an example of a diagram illustrating an attachment structure of a pusher according to a fifth embodiment.

FIG. 11 is a diagram illustrating an attachment structure of the pusher 19, according to the fifth embodiment. Specifically, FIG. 11 is a sectional view corresponding to FIG. 6.

In an example, the fixing portion 20D is a member that can fixe the pusher 19 to the protruding portion 1631, similarly to the fixing portion 20C described above with respect to the third embodiment. In this fifth embodiment, the fixing portion 20S is or can include a pin.

The fixing portion 20D can be fixed to the pusher 19 in a posture where the fixing portion 20D bridges between the pair of inclined surfaces 195, after the pusher 19 has been attached to the protruding portion 1631. That is, this structure disables detachment of the pusher 19 from the protruding portion 1631 by the protruding portion 1631 getting caught on the fixing portion 20D.

The fifth embodiment described above has effects similar to those of the above described first embodiment. The fifth embodiment has the structure in which the fixing portion 20D prevents the pusher 19 from being detached from the protruding portion 1631. Therefore, the structure enables prevention of remanufacturing of the treatment tool by a person unrelated to a manufacturer that remanufactures the treatment tool.

Other Embodiments

Some embodiments of the disclosure have been described thus far, but the disclosure is not to be limited only to the above described first to fifth embodiments.

In each of the above described first to fifth embodiments, the treatment tool according to the disclosure is configured to apply both ultrasound energy and high frequency energy to a target site, but without being limited to this configuration, the treatment tool may be configured to apply at least one of ultrasound energy, high frequency energy, and thermal energy. "Applying thermal energy to a target site" herein means transmitting heat generated in a heater, for example, to a target site.

In each of the above described first to fifth embodiments, the inner pipe 14 is adopted as the tubular portion, but the tubular portion is not necessarily the inner pipe 14. The outer pipe 13 may be adopted as the tubular portion. That is, the jaw 11 may be configured to be opened and closed by movement of the outer pipe 13 along the central axis Ax.

In the above described first embodiment, the pusher 19 that is elastically deformable is adopted as the pusher, but without being limited to the pusher 19, any other fixation tool, such as a screw, may be adopted as the pusher.

In the above described first embodiment, the number of the pushers 19 adopted is just one, but without being limited to one, the number of the pushers may be plural. In a case where a plurality of the pushers is adopted, the pushers are respectively provided at positions where the pushers press the inner pipe 14 toward the central axis Ax.

In the above described first embodiment, the path heading from the opening 193 to the fitting recessed portion 194 in the pusher 19 is a linear path along the attachment direction Ar3, but the path is not limited to this linear path, and may be a curved path or an L-shaped path.

A treatment tool according to the disclosure enables improvement in ease of assembly. Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A medical treatment instrument, comprising:

an end effector comprising an ultrasonic blade;

a tube coupled to the end effector;

a driver coupled to a proximal end of the tube, wherein the driver is configured to actuate the end effector via the tube, and wherein the driver includes a protrusion protruding toward a distal end of the tube; and a pusher configured to support a coupling between the tube and the driver, wherein the pusher is configured to prevent a movement of the tube relative to the driver in a longitudinal direction of the tube, and wherein the pusher is located between the tube and the protrusion in a radial direction of the tube; and wherein the pusher comprises:

a base;

a first protrusion; and a second protrusion, wherein the first protrusion and the second protrusion are extended from the base in a width direction intersecting with the longitudinal direction of the tube, and wherein the first protrusion is located between the protrusion and the tube.

2. The medical treatment instrument according to claim 1, wherein the pusher is formed in a U-shape.

3. The medical treatment instrument according to claim 1, wherein the tube includes a notch, wherein the driver includes a projection, and wherein the notch is connected to the projection.

4. The medical treatment instrument according to claim 1, further comprising:

a vibration transmission portion located inside the tube, wherein the vibration transmission portion is configured to transmit ultrasound vibration.

5. The medical treatment instrument according to claim 2, wherein the pusher comprises:

a pin, wherein the first protrusion and the second protrusion sandwiches the protrusion, and wherein the pin is fixed between the first protrusion and the second protrusion.

6. The medical treatment instrument according to claim 1, wherein the pusher is configured to be adhered to at least one of the driver or the tube.

7. The medical treatment instrument according to claim 1, wherein the driver is configured to move along a longitudinal axis of the medical treatment instrument.

8. The medical treatment instrument according to claim 1, wherein the pusher is configured to be attached to the protrusion.

9. The medical treatment instrument according to claim 3, wherein the projection is located inside the notch.

10. The medical treatment instrument according to claim 3, wherein the projection is located opposed to the protrusion.

11. The medical treatment instrument according to claim 3, wherein the tube is located between the projection and the protrusion.

12. The medical treatment instrument according to claim 3, wherein the pusher is located between the projection and the protrusion.

13. The medical treatment instrument according to claim 1, wherein the first protrusion and the second protrusion sandwiches the protrusion.

14. The medical treatment instrument according to claim 1, wherein the pusher contacts an outer surface of the tube.

15. The medical treatment instrument according to claim 14, wherein the pusher contacts an outer surface of the protrusion.

* * * * *